United States Patent [19]

Tsantrizos et al.

[11] Patent Number: 5,100,456
[45] Date of Patent: Mar. 31, 1992

[54] HERBICIDAL METABOLITES OF PHOMOPSIS CONVOLUVULUS FOR THE EFFECTIVE CONTROL OF FIELD BINDWEED

[75] Inventors: Youla S. Tsantrizos, Ville St-Laurent; Kelvin K. Ogilvie, Canning; Alan K. Watson, Pincourt, all of Canada

[73] Assignee: Royal Institution for the Advancement of Learning (McGill University), Montreal, Canada

[21] Appl. No.: 552,243

[22] Filed: Jul. 12, 1990

[51] Int. Cl.$^5$ .................... A01M 43/08; C07D 307/88
[52] U.S. Cl. ........................ 71/88; 549/307; 549/310
[58] Field of Search ............... 549/307, 310; 71/88; 514/470

[56] References Cited

U.S. PATENT DOCUMENTS 2,811,535 10/1957 Wheeler et al. .................. 71/88

OTHER PUBLICATIONS

Achenbach, H., et al., *Chemical Abstracts* 97: 178408e, "Metabolite of Microorganisms," pp. 454–455 (1982).
Ichihara; A., et al., *Chemical Abstracts* 103: 83122k "Dihydrogladiolic acid, another phytotoxin . . .," p. 195 (1985).
Teijin, *Chemical Abstract* 102: 113271g, abstract of Jp 59–163,378, "Gladiolic acid derivatives," p. 691 (1985).
Overeem, J. et al., *Chemical Abstracts* 62: 5237a–b, "Mollisin, a naturally occurring chlorine-containing quinone," (1965).
Brown, J. J., et al., *J. Chem. Soc.*, "Phthalaldehydes and Related Compounds," pp. 1285–1289 (1953).

*Primary Examiner*—Richard L. Raymond
*Assistant Examiner*—Mark W. Russell
*Attorney, Agent, or Firm*—Dressler, Goldsmith, Shore, Sutker & Milnamow, Ltd.

[57] ABSTRACT

The invention relates to the isolation, characterization and application of a bioherbicide composition characterized by its phytotoxcity towards the agricultural pest *Convolvulus arvensis* (field bindweed) and the aquatic weed *Lemna paucicostata*. The composition consists of a compound of formula I:

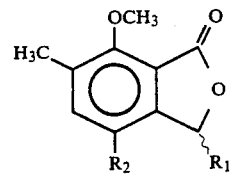

wherein $R_1$ is selected from H and OH, and $R_2$ is selected from $-CH_2OH$ and $-COOH$, salts and esters thereof, in association with an agriculturally acceptable carrier. The herbicide of this invention can be used for the control of field binweed and potentially other pest plants.

8 Claims, No Drawings

HERBICIDAL METABOLITES OF PHOMOPSIS CONVOLUVULUS FOR THE EFFECTIVE CONTROL OF FIELD BINDWEED

BACKGROUND THE INVENTION

The perennial plant *Convolvulus arvensis*, better known as field bindweed or wild morning glory, is a serious agricultural problem around the world with the exception of the tropics. Field bindweed infestations are encountered along roadsides, in city green spaces and cultivated lands throughout most of the U.S. and Canada and it has been classified as one of the most important weeds worldwide.

Phenoxy herbicides such as (2,4-dichlorophenoxy)acetic acid (2,4-D), (4-chloro-2-methylphenoxy)acetic acid (MCPA) and 3,6-dichloro-2-methoxybenzoic acid (DICAMBA) are presently used for the control of this pest. Although, these compounds are among the most effective and commonly used herbicides they are generally costly and ineffective in suppressing the spreading of bindweed. For example, in California, field bindweed is more prevalent now than 20 years ago in spite of the intensive control programs used.

In the early 1970's, a number of independent studies on the biological control of field bindweed were initiated.

Among them, insects and gall mites were considered but were found to be inadequately host-specific causing damage to crop plants in addition to the weeds.

Fungi which are pathogenic to field bindweed present an alternate possibility for its biological control. *Phomopsis convolvulus*, an organism which was isolated and identified recently by Ormeno-Nunez et al (*Plant Dis.*, 1988, 72, 338 and *Can. J. Bot.*, 1988, 66, 2228) is one such pathogen. The *Phomopsis convolvulus* has been deposited in The Commonwealth Mycological Institute in Kew, England and assigned the accession number IMI 303662. It has been shown to infect field bindweed causing brown lesions which sometimes are surrounded by yellow haloes characteristic of phytotoxin production.

In general, the genus Phomopsis includes several pathogenic fungi which cause a variety of disease symptoms to plants, animals and occasionally humans. The majority of these microorganisms have not yet been thoroughly investigated and only a few are known to produce biologically active metabolites. Among these metabolites are the cytochalasins, which are mammalian toxins exhibiting a number of unusual effects on animal cells, sometimes plant cells, and on microbial cells. Other biologically active metabolites from Phomopsis fungi include the ionophoric mycotoxin phomopsin A isolated from *Phomopsis leptostromi* and several insect deterrent metabolites of *Phomopsis oblonga*.

However, a herbicidal metabolite effective against field bindweed has never been isolated before from a Phomopsis fungus or any other source. In addition, since *Phomopsis convolvulus* is a host-specific pathogen of field bindweed it would be highly desirable if any metabolite responsible for its pathogenicity on this agricultural pest produced therefrom, could be isolated and identified.

SUMMARY OF THE INVENTION

In accordance with the present invention, the phytotoxic metabolites obtained from the fungus *Phomopsis convolvulus* have now been separated and identified and the bioherbicidal activity of each metabolite against field bindweed has also been evaluated.

More specifically, the phytotoxic metabolite of the present invention are derived from the fungus *Phomopsis convolvulus* and correspond to the general formula I:

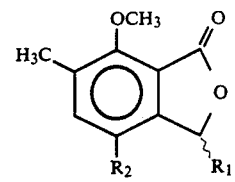

wherein when $R_1$ is selected from hydrogen and hydroxy; and $R_2$ is selected from $-CH_2OH$ and $-COOH$, with the proviso that when $R_1$ is hydroxy $R_2$ is COOH and salts and esters thereof.

With the isolation of phytotoxic metabolites of *Phomopsis convolvulus* novel compounds possessing superior herbicidal properties are provided and unlike the fungus itself, they are stable, have a consistent level of toxicity and require no maintenance. The use of the novel metabolites of the present invention as herbicides is not only more convenient but also has a broader spectrum of utility than the fungus itself.

The present invention is also concerned with herbicidal composition wherein a herbicidal amount of any of the compounds of Formula I, mixtures thereof and salts or esters thereof are combined with an agriculturally acceptable inert carrier for application to the undesirable agricultural pest *Convolvulus arvensis* (field bindweed) and a few closely related plant species.

Also within the scope of the invention is a method for eradicating bindweed by applying thereto a phytotoxic amount of one of the compounds of Formula I, or a mixture thereof or salts or esters thereof.

It will be readily appreciated that the isolated herbicides of Formula I provide appreciable advantages over the use of spores of the *Phomopsis convolvulus* as a mycoherbicide. For example, the individual novel herbicides of the present invention have a longer life and require much less storage space, the logistics of formulation and application are simpler, there is no danger of disease spread to nontarget species, results are not dependent on environmental conditions, the efficacy of particular application rates can be more accurately predicted and finally they can be produced at a lower cost.

The novel products of the present invention may also be used in the form of salts or esters thereof. As an example of suitable salts there may be used the sodium, potassium, ammonium, triethylamine or triethanolamine salts. As suitable esters, there may be mentioned the alkyl esters such as the methyl, isopropyl, butyl or octyl esters or the heavy or low volatile esters such as the butoxyethanol ester, the propyleneglycolbutylether ester or the tetrahydrofurfuryl ester.

In addition, determination of the chemical structure and relative herbicidal activity of the above metabolites, permits attempts to be made towards the synthetic preparation of these natural products. Furthermore, the investigation of the relationship between structure and relative toxicity of the three compounds is useful as a guide for the synthesis of commercially more suitable herbicidal analogues.

Other advantages of the present invention will be readily illustrated by referring to the following description.

DETAILED DESCRIPTION OF THE INVENTION

The novel compounds of the present invention are the 4-carboxy-3-hydroxy-7-methoxy-6-methyl-1(3H)-isobenzofuranone (IA), the 4-(hydroxymethyl)-7-methoxy-6-methyl-1(3H)-isobenzofuranone(IB) and the 4-carboxy -7-methoxy-6-methyl-1(3H)-isobenzofuranone (IC) as shown in formula I and are obtained from the growth medium of the fungus *Phomopsis convolvulus* through the isolation and purification methodology hereinafter described.

A suitable herbicidal composition provided by the present invention comprises one of the above novel compounds or mixtures thereof in association with an inert carrier.

Since the compounds presented in this invention exhibit different strengths and different symptoms of phytotoxic activity, the effective concentrations in a given preparation would vary and depend on which compounds are used. Details on the phytotoxic activity of each compound are described hereinafter.

As carrier, the active ingredients may be applied as a dust, a wettable powder, dry flowable powder, emulsifiable concentration, solution or similar formulation or applied as a granular material or a spray, to the site of the bindweed and other material. The inert carrier can be any carrier presently used to apply herbicides to plants.

In a further aspect of the present invention, there is provided another compound which has been isolated from the *Phomopsis convolvulus* fungus. This new compound is the 3-(4-methoxy-3-methyl-α-pyron-6-yl)2-methyl-2-butenoic acid corresponding to the formula II:

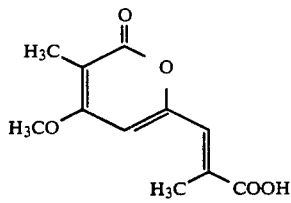

This compound is effective against *Lemna paucicostata* and may be used in association with an inert carrier well known in this field.

EVIDENCE OF UTILITY

The ideal assay for determining the toxicity of a compound to plant tissues would be a large scale screening process of the type utilized by major herbicide industries. This process involves pre- and postemergence applications of the test compound on dozens of crop and weed plants in the well controlled environment of a green house.

In natural product research, such an approach is not feasible due to the minute amounts of metabolites usually isolated. Although a number of bioassay techniques requiring small quantities of material are available, most of them are inadequate in testing all aspects of phytotoxic activity. To further complicate testing, phytotoxicity manifests itself in a variety of different ways. The symptoms can include inhibition of seed germination, seedling growth, photosynthesis, chloroplast development, leakage of electrolites, wilting and others.

External factors may also influence the toxicity of a test compound. For example, the plant species, the physiological growth stage, the age of the test tissue, the environmental conditions, and even the existence of a synergistic compound are all factors which have been shown to affect the results of a bioassay.

The phytotoxic activity of the compounds of this invention was evaluated using the aquatic plant Lemna and plant tissues of field bindweed. The usefulness of Lemna plants in phytotoxicity bioassays has been demonstrated by Einhellig et al (*J. Chem. Ecol.*, 1985, 11, 65). The Lemna species *L. paucicostata* was chosen for testing the *P. convolvulus* metabolites and standardized growth conditions suitable for biochemical experimentation were followed according to procedures in *Plant Physiol.*, 1985, 65, 906.

In all bioassays the metabolites (or metabolite mixtures) were dissolved in absolute ethanol, then aliquotes of those solutions (50-5 μL) were added to Lemna nutrient broth or doubly distilled water to make the final test samples.

The toxicity of ethanol to *L. paucicostata* and field bindweed tissue was initially evaluated. In leaf-puncture bioassays of field bindweed, toxicity was not observed at concentrations of ethanol up to 2% in water. With *L. paucicostata* plants, growth inhibition and chlorosis were observed when the concentrations of ethanol was greater than 1% (v/v) of the total nutrient medium. Hence, all bioassays were performed with test solutions containing less than 1% ethanol in either Lemna nutrient medium or doubly distilled water. In few cases where crude samples were tested using higher than 1% concentration of ethanol (in order to solubilize samples) a control sample of equal ethanol content was always used. Since in all cases the concentration of ethanol in the control was the same as that of the most concentrated test sample, any observation of phytotoxicity was compared to the control before it was considered to be reliable. The concentrations at which each of the pure metabolites was tested varried, depending on the solubility of the compound in an aqueous system and the availability of material A large number of Lemna fronds (25-30) and bindweed leaves (5-6) was used in each test in order to increase the reliability of the results obtained. In all cases, the observations made with the Lemna bioassays were consistent with the results obtained from the leaf-puncture bioassays.

In leaf-puncture bioassays, field bindweed cuttings (5-8) which were either punctured with the tip of a fine needle, cut along the middle vein of the leaf or just cut at the petiole (no injury to the leaf tissue), were placed on a filter paper and soaked with the test solution in a Petri dish. The leaf tissues were inspected for several days after for the development of brown or yellow spots and wilting.

The bioassays of the pure compounds (compounds IA, IB and IC) were carried out only at those concentrations where a true solution could be obtained using a concentration of ethanol lower or equal to 1% of the total volume of the test sample.

Metabolite IC was found to be the most potent phytotoxin, causing total inhibition of growth and 100% chlorosis of the Lemna tissues within 12 hours at concentrations of $5.9 \times 10^{-4}$M and within 24 hours at concentrations of $3.5 \times 10^{-4}$M.

The less toxic metabolites IA and IB were found to inhibit the growth of Lemna plants by approximately 50% and 30% respectively at concentrations of $5\times10^{-4}$M.

The phytotoxic effects of all three metabolites on field bindweed were evaluated using leaf-cuttings from plants 3–4 weeks old, using only the top two leaves on young shoots. For each assay an average of 5–6 leaves were cut, with a scalpel under water, at the base of the stem and placed on a moist piece of filter paper (0.5 mL doubly distilled $H_2O$) in a Petri dish. The phytotoxic metabolite samples, dissolved in absolute ethanol, were diluted to a total volume of 2 mL using doubly distilled water. The most concentrated sample of each assay had an ethanol content of 1%, hence, the control solution was also an 1% ethanol solution in water. A)1 leaves Were rinsed with the test solutions and incubated under a grow-lamp for a period of one week. Toxic symptoms of wilting and browning were observed with metabolite IC after four hours at concentrations of $5.9\times10^{-4}$M and $3.5\times10^{-4}$M. Twelve hours later, these same symptoms appeared on the leaves exposed to metabolite IA at concentrations of $5\times10^{-4}$M but they were not seen at all with metabolite IB, even after several days.

The extent of browning of the bindweed leaves did not seem to progress very much after the first 24 hours. A possible explanation for this phenomenon could be the death of cells around the base of the leaf and the injured areas which would effectively stop absorption and, hence, prevent the further uptake of the toxins. In order to partly test this hypothesis several young bindweed shoots (about 2" long) were placed in solution of the less potent phytotoxic metabolite IA, at a concentration of about $5\times10^{-4}$ and $2\times10^{-3}$ M. It was assumed that metabolite IA will have a less pronounced and a less immediate effect on the injured cells, permiting its own absorption and delivery throughout the cutting's tissue. A solution of 1% ethanol in water was used as the control and both sets of plants were observed and compared over a period of 5–6 days. After 40–48 hours the plants exposed to the toxin displayed obvious signs of wilting, although they showed some recovery 20–24 hours later. At the end of the observation period (5–6 days later) the systemic absorption and toxicity of metabolite IA was very clear, as the leaves of the treated plants were almost completely wilted where the plants in the control solution did not show any such symptoms.

In conclusion, the physiological effects observed on field bindweed when infected with *P. convolvulus* were shown to be chemically mediated. The biological activity of metabolites IA and IC and to a lesser extent IB clearly demonstrates that they play an important role in the development of the phytotoxic symptoms. These compounds are, to the best of our knowledge, novel compounds. It is therefore conceivable that these compounds or their synthetic analogues could provide the agriculture industry with an effective herbicide for the control of field bindweed and perhaps other weed plants.

ISOLATION

General Isolation Scheme for the Herbicidal Metabolites of *P. convolvulus*

Moist barley grains were inoculated with a conidia suspension of *Phomopsis convolvulus* and incubated at room temperature for 28–30 days. At the end of the growth period the infected grains were washed for several hours with excess water in order to extract the extracellular metabolites of this fungus. The overall general scheme outlined in Table was subsequently followed in order to eliminate biologically inactive components and partition the remaining crude into a non-polar fraction, containing a number of steroid compounds, and a polar fraction, containing most of the phytotoxic metabolites.

The aqueous crude was filtered through a few layers of cheese cloth and centrifuged to remove the grains, mycelia and newly formed conidia. The liquid culture was then reduced to about 10% of its original volume and freeze-dried to give a very fine, light-grey, powder. Upon extraction with methanol this powder was partitioned into a biologically phytotoxic methanolic extract and a white solid void of any observable activity. The methanolic crude was evaporated to a brown gum, which was suspended in a small volume of water, acidified to pH of about 3 and extracted several times with ethyl acetate. The ethyl acetate extract was found to exhibit strong phytotoxic activity. Insignificant activity was observed with the aqueous extract.

The above phytotoxic crude was then suspended in methylene chloride and extracted with a saturated solution of $NaHCO_3$. The bicarbonate layer was reacidified with dilute HCl solution to pH of about 2.5–3, reduced in volume under high vacuum and extracted with ethyl acetate. Leaf-puncture bioassays indicated than most of the biological activity was extracted into the basic aqueous layer and only very weak activity was observed with the methylene chloride extract. Further purification of this latter extract (crude Pc 4 of Table 1) led to the isolation of the weakly phytotoxic steroid ergosterol peroxide.

TABLE 1

General isolation schemes of Phomopsis metabolites

Barley grains (infected with *P. convolvulus*)

a) soak in $H_2O$ (12 hr.)
b) filter through cheese cloth
c) Centrifuge and decant aqueous layer
d) Evaporate to dryness ---> Pc 1(1)
c) Stir Pc 1 in methanol for 2 h, at 45-50° C.
d) Filter Methanol solution ---> Pc 2(1) Solid a) Evaporate to dryness
b) Dissolve Pc 2 in $H_2O$
c) Acidify to pH 3 with 0.1N HCl
d) Extract with ethyl acetate Ethyl acetate layer ---> Pc 3(1) Aqueous layer

TABLE 1-continued
General isolation schemes of Phomopsis metabolites

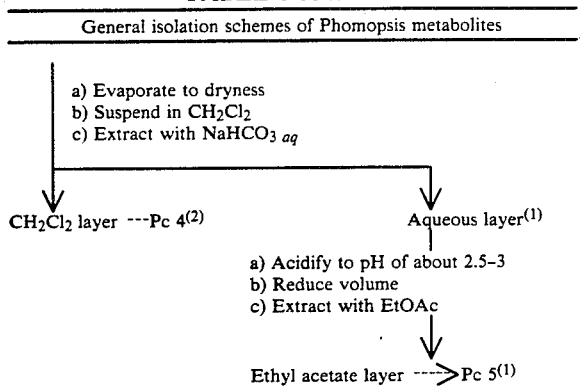

(1) Strong phytotoxicity observed
(2) Weak phytotoxicity observed

Purification of Metabolites IA, IB and IC from the Herbicidal Crude Pc 5 of *P. convolvulus*

Isolation and HPLC analysis

Purification of the phytotoxic crude Pc 5 (Table 1) proved to be exceedingly difficult and totally unsuccessful using either silica or cellulose chromatography. Flash column chromatography, however, using reverse phase silica gel led to a moderate separation of the components. The reverse phase silica was prepared using the methodology developed by Evans and co-workers (*Chromatographia*, 1980, 13, 5).

The metabolite mixture Pc 5, from *P. convolvulus*, was thus partitioned via reverse phase flash chromatography using the solvent gradient outlined in Table 2. All fractions (of about 20 mL volume) were assayed for biological activity using leaf-puncture bioassays and Lemna plants. The results obtained are noted in Table 2.

TABLE 2
Reverse phase flash chromatography of crude Pc 5

| Solv. (v/v in mL) | Activity | Solv. (v/v in mL) | Activity |
|---|---|---|---|
| $H_2O$ (25) | — | $CH_3OH$ (25) | — |
| $H_2O$ (25) | — | $CH_3OH/CH_2Cl_1$ (23/2) | — |
| $H_2O/CH_3OH$ (23/2) | — | $CH_3OH/CH_2Cl_2$ (20/5) | — |
| $H_2O/CH_3OH$ (20/5) | — | $CH_3OH/CH_2Cl_2$ (15/10) | — |
| $H_2O/CH_3OH$ (15/10) | ++ | $CH_3OH/CH_2Cl_2$ (10/15) | — |
| $H_2O/CH_3OH$ (10/15) | +++ | $CH_3OH/CH_2Cl_2$ (5/20) | — |
| $H_2O/CH_3OH$ (5/20) | + | $CH_3OH/CH_2Cl_2$ (2/23) | — |
| $H_2O/CH_3OH$ (2/23) | — | $CH_2Cl_2$ (25) | — |

Biological activity observed: — none, + weak, ++ moderate, +++ strong

In hope of achieving better separation of the phytotoxic metabolites, the above procedure was repeated collecting much smaller volume fractions (about 8 mL) and changing the polarity of the solvent system even more gradually. Due to the small amounts of available sample, the new fractions were not assayed for biological activity. Instead, their chemical composition was compared to the phytotoxic fractions previously isolated (Table 2) by thin layer chromatography (TLC). Fractions 18 to 21 appeared to have the same composition as the crudes found to be active, hence, they were further analyzed by HPLC chromatography.

Metabolites IA and IB were isolated from the combined fractions 18-19 after HPLC chromatography on a C18 reverse phase column eluted with 59.8% $H_2O$, 40% $CH_3OH$, 0.2% $CH_3COOH$. Their respective retention times were 22-23 minutes and 16-17 minutes after the void volume, at a flow rate of 2 mL/min. Metabolite IB was re-chromatographed using the same column and flow rate but a solvent mixture of 54.1% $H_2O$, 45.8% $CH_3OH$, 0.1% $CH_3COOH$ in order to obtain a high purity sample. Under these conditions, it eluted 10-11 minutes after the void volume.

Metabolite IC was isolated from the combined fractions of 20-21 after HPLC chromatography on a C18 reverse phase column. The compound was eluted using a solvent mixture of 54.4% $H_2O$, 45.4% $CH_3OH$, 0.2% $CH_3COOH$ at a flow rate of 2 mL/min. Its retention time was 27-29 minutes after the void volume.

STRUCTURE DETERMINATION

Identification of the Metabolite 4-carboxy-3-hydroxy-7-methoxy-6-methyl-1(3H)-isobenzofuranone (IA)

The $^1H$ NMR of metabolite IA strongly suggested an aromatic or other unsaturated type of molecule. There were only four easily distinguishable substituents, a methyl group at 2.35 ppm, a methoxy group at 4.14 ppm and two single protons at 6.91 and 8.09 ppm. The solubility of this compound in non-protic NMR solvents was very poor, hence, information on the presence of any exchangeable protons could not be easily obtained.

Since coupling was not observed between any of the protons on the molecule, NMR experiments using Nuclear Overhauser Enhancement (NOE) effects were carried out in an attempt to gain information on the relative positions of the four substituents and results are shown in Table 3. A positive NOE effect was observed between the methoxy and the methyl groups, and between the methyl and the proton at 8.09 ppm. The proton at 6.91 ppm did not exhibit an NOE effect with any of the other protons, suggesting that its position on the molecule was remote from the other substituents.

TABLE 3
Nuclear Overhauser Enhancement in the $^1H$ NMR (300 MHz, acetone-$d_6$) spectrum of IA.

| Saturated Signal ($\delta$) | Observed enhancement ($\delta$) |
|---|---|
| 2.35 (9-CH3) | 4.14 (10-OCH3, 10%), 8.09 (H5,4%) |
| 4.14 (10-OCH3) | 2.35 (9-CH3, 14%) |
| 8.09 (H5) | 2.35 (9-CH3, 14%) |

The $^{13}C$ NMR showed the presence of eleven different types of carbons. The presence of a methyl (15.7 ppm) and a methoxy (62.6 ppm) group, both attached to an $sp^2$-hybridized carbon, were confirmed. APT NMR showed seven of them to be quaternary carbons at 166.4, 165.7, 160.5, 149.4, 134.3, 121.9 and 118.3. The remaining two signals (139.3 and 97.4 ppm) were shown to be tertiary, through a DEPT experiment, and were assigned to the carbons carrying the single protons at 8.09 and 6.91 ppm respectively.

The chemical shift of the carbon at 97.4, as well as the chemical shift of its proton (6.91 ppm), indicated a —O—CH—O— moiety as a possible part of this molecule. From the quaternary carbons, the two signals at 166.4 and 165.7 were thought to be carbonyl carbons of either an acid or an ester. The downfield signal at 160.5 ppm is characteristic of aromatic carbons attached to a hydroxy or methoxy group, hence, it was tentatively assigned as such and connected to the methoxy substituent. The rest of the carbons were tentatively assigned to four carbons of a benzene ring.

Most of the $^{13}C$ NMR experiments had to be conducted at very low temperatures ($-45°$ to $-55°$ C.) since it was noted that the signals at 165.7 and 121.9 ppm were very broad when the normal $^{13}C$ NMR spectra was recorded at room temperature and they were almost nonobservable in the APT NMR. However, in low temperature NMR experiments ($-45°$ to $-55°$ C.) these signals were observed without any difficulty.

Such an effect usually indicates the existence of two equilibrium structures with a fast exchange taking place at room temperature In cases where the equilibrium constant permits both structures to exist in significant amounts, two separate sets of signals may be observed by carrying out the NMR experiments at sufficiently low temperature. This was not the case with metabolite IA. The presence of a carboxylic acid moiety attached to an aromatic carbon was proposed as a possible explanation for the results obtained with this compound. In such molecules a very small degree of dissociation of the acidic proton often causes the broadening of both the carbonyl carbon (165.7 ppm) and the carbon to which it is directly attached (121.9 ppm).

The IR spectra of metabolite IA showed an OH absorption at 3381 $cm^{-1}$, —C≡C— absorption at 1613 $cm^{-1}$, and two carbonyl absorptions at 1728 and 1773 $cm^{-1}$ due to a carboxylic acid and a five-membered ring conjugated lactone. Literature IR values of lactones fused to a benzene ring were in full support of the phthalide type structure proposed (structure of IA shown previously).

Chemical ionization ($NH_3$) mass spectrometry gave an ion at 256 ($M^+ + NH_3$) with relative intensity of 100%, a molecular ion of 239 ($M^+ + 1$) with relative intensity of 53%, and two other ions both produced by the loss of —CHO at 227 [$M^+ + NH_3$—(—CHO)] and at 209 [$M^+$—(—CHO)]. These results supported an elemental composition of $C_{11}H_{10}O_6$ for this compound.

Based on all of the above data, two structures, IA and IX, were considered possible for this metabolite. Final proof, however, in support of structure IA was obtained through the data of low temperature $^1H$—$^{13}C$ coupled NMR experiments and literature $^{13}C$ NMR values of related compounds.

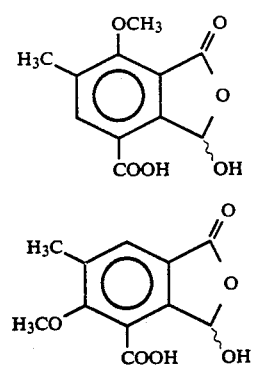

In the fully coupled spectra of this metabolite (300 MHz, at $-52°$ C.), large coupling constants characteristic of $^1J$ values were observed for the signals at 139.3, 97.4, 62.6 and 15.7 ppm as expected. The signal at 139.3 ppm appeared as a doublet of quartets due to additional long-range coupling with the protons of the methyl group ($^1J=162$ Hz, $^3J=5$ Hz). Similarly, the methyl group at 15.7 ppm appeared as a quartet of doublets ($^1J=128$ Hz, $^3J=5$ Hz) which collapsed to a simple quartet upon decoupling of the aromatic proton at 8.09 ppm. The expected results were also obtained with the signal at 97.4 ppm, which was assigned to the C-3 carbon. This carbon (C-3) appeared as a doublet ($^1J=179$ Hz) in the coupled spectra but changed to a singlet when the proton at 6.91 ppm was decoupled. The quaternary carbons at 121.9 and 118 3 ppm were singlets in all spectra and they were assigned to C-4 and C-7a respectively. Although, the reverse assignment could be argued for these two signals, the broadness of the 121.9 peak in the room temperature NMR spectrum, is believed to be due to the attached ionizable carboxylic acid. The quaternary multiplets at 134.2 and 160.5 ppm were assigned to C-6 and C-7 respectively in structure IA or C-6 and C-5 in structure IX, since both of them showed long-range coupling with the methyl and methoxy protons.

The splitting pattern of the remaining quaternary carbons were anticipated to show enough differences between structures IA and IB so as to provide proof for the identity of this metabolite. Several small but important differences in the coupling patterns of these two structures were expected. For example, coupling between the aromatic proton (H5 or H7) and the lactone carbonyl was believed unlikely in structure IA but it was expected in structure IX. $^3J$ coupling constants between substituents of a benzene ring are usually of the order of 5–7 Hz. The opposite results were anticipated for the coupling of the carboxylic acid carbon and the aromatic proton. $^3J$ coupling would be expected in structure IA between H5 and C-8. However, such coupling would be unlikely in structure IX, H7 to C-8, since coupling between protons and carbons separated by more than three bonds is rare and their coupling constants decrease in value with increasing distance (e.g. $^4J=0-1.5$ Hz). On the other hand, $^3J$ coupling between the aromatic proton (H5 or H7) and C-3a, and between H3 and C-1 (the lactone carbonyl) would most likely be observed with either structure. The coupling constant of the latter signal (C-1 signal coupled to H3) is less predictable and, as in all other cases, would depend on the dihedral angle between H3 and the lactone carbonyl.

Both of the carbonyl carbons and the C-3a signal appeared as doublets in the fully coupled spectra. Selective decoupling of the aromatic proton (8.09 ppm) led to the collapse of the doublet at 149.4 ppm (C-3a) as expected, and of the carboxylic acid doublet at 165.7 ppm but had no effect on the doublet of the lactone (166.4 ppm, $^3J=4$ Hz). However, selective decoupling of the proton at 6.91 ppm (H3) affected both carbonyl carbons, changing the lactone into a sharp singlet and the acid into a broad singlet. The broadness of the latter signal was due to the coupling between the acid and the aromatic proton (H5). These results were in strong support of IA as the correct structure for this metabolite. A summary of all the data obtained from these experiments is given in Table 4.

A literature search for compounds structuraly related to metabolite IA revealed, among others, the natural product 4-formyl-3,5-dihydroxy-7-methoxy-6-methyl-1(3H)-isobenzofuranone. This metabolite was isolated by Achenbach et al from the fungus *Aspergillus duricaulis* and shown to possess antibacterial properties (Z. Naturforsch, 1982, 37B, 1091).

Considering the close structural similarities between the two compounds, it was assumed that approximate $^{13}C$ chemical shifts for metabolite IA could be calculated from those of the above literature compound. The empirical parameters normally used for the calculation of chemical shifts in a substituted benzene ring were added to the reported values of the literature compound. For example, the reported chemical shift for C-5 of the compound 4-formyl-3,5-dihydroxy-7-methoxy-6-methyl-b 1(3H)-isobenzofuranone was 166.0 ppm. To this value, the affects of an —OH group directly attached (−26.9 ppm), and of an ortho aldehyde (−1.3 ppm) were removed, where the affect of an ortho carboxylic acid (+1.5 ppm) was added. The empirical chemical shift obtain from this calculation (139.3 ppm) was identical to that observed for the C-5 carbon of metabolite IA. All other calculated values were within 0 to 3 ppm from actual shifts and they are shown in Table 4.

It is also interesting to note, that metabolite IA did not exhibit any optical activity. The spontaneous racemization of 3-hydroxylactones through ring-chain tautomerism is a well known phenomenon which has been reported for many compounds. In an analogous fashion, metabolite IA is believed to exist in equilibrium with its aldehyde-carboxylic acid tautomer.

The $^{13}$C NMR data of several other naturally occurring phthalides and synthetic compounds was also considered. All evidence was consistent with the assignment of IA as indicated and a complete set of data for this compound is given in the Experimental data provided hereinafter.

bons were observed, one of which was an sp$^2$-hybridized —CH (137.2 ppm), two were secondary carbons (—CH$_2$, 62.2 and 70.1 ppm), one methoxy (62.5 ppm) and one methyl (15 4 ppm), as it was indicated by its DEPT NMR. From the remaining six quaternary carbons only one had the appropriate chemical shift for a carboxylic acid or lactone (171.2), four signals had chemical shifts very close to those of C-3a, C-6, C-7 and C-7a of metabolite IA and one was approximately 10 ppm downfield from the C-4 carbon of metabolite IA. It was also noted, that the room temperature $^{13}$C NMR spectra of IB did not show any broad signals neither was it any different when recorded at low temperature. This observation, coupled with the fact that a carbonyl carbon was lost and a —CH$_2$—OH gained in going from the spectra of metabolite IA to that of IB suggested the reduction of the carboxylic acid to a primary alcohol. The 10 ppm shift of the C-4 carbon would also be expected if that was the case.

The IR (CHCl$_3$) data of metabolite IB was consistent with the proposed loss of the carboxylic acid and showed absorptions for only one carbonyl, that of the lactone at 1762 cm$^{-1}$, of an alcohol at 3630 and 3540 cm$^{-1}$ and of double bonds at 1600 cm$^{-1}$.

High resolution, chemical ionization (NH$_3$), mass spectrometry gave a molecular ion of 209.0814 (M$^+$+1) suggesting an elemental composition of C$_{11}$H$_{12}$O$_4$ for this compound (calculated mass: 209.0814).

TABLE 4

| $^{13}$C NMR (300 MHz, acetone-d$_6$, −52° C.) of metabolite IA | | | | | |
|---|---|---|---|---|---|
| C | decoupled δ | calculated δ | coupled | H3 coupled | H5 coupled |
| 1 | 166.4 | −167 | d; $^3J_{C-H3}$ = 4 Hz | s | d |
| 8* | 165.7* | — | d; J = ~ 2.5 Hz | s(br) | s(sh) |
| 7 | 160.5 | 161.6 | m; | m | m |
| 3a | 149.4 | 152.5 | d; $^3J_{C-H5}$ = 7.7 Hz | d | s |
| 5 | 139.3 | 139.3 | d,q; $^1J$ = 162 Hz d; $^3J_{C-H9}$ = 5 Hz | d,q | q |
| 6 | 134.2 | 133.6 | q; $^2J_{C-H9}$ = 6 Hz | q | q |
| 4* | 122* | 119–124 | s | s | s |
| 7a | 118.3 | 117.7 | s | s | s |
| 3 | 96.0 | 96.0 | d; $^1J$ = 179 Hz | s | d |
| 10 | 62.7 | 63.1 | q; $^1J$ = 146 Hz | q | q |
| 9 | 15.7 | — | d,q; $^1J$ = 128 Hz $^3J_{C-H5}$ = 5 Hz | d,q | q |

*broad signals at room temperature
broad signal due to $^4$J coupling between C-8 and H3 of ~1-2 Hz Identification of the Metabolite 4-(hydroxymethyl)-7-methoxy-6-methyl-1(3H)-isobenzofuranone (IB)

Metabolite IB was sufficiently soluble in deuterated chloroform to permit a complete proton spectra to be observed. As in the case of metabolite IA, a methyl and a methoxy group were present, at 2.26 and 3.90 ppm respectively. An exchangeable, very broad signal (1H) was observed at 2.6–2.7 ppm which was coupled to a doublet (2H, J=6 Hz) at 4.66 ppm. The extreme broadness of this signal (believed to be an —OH) indicated further, long-range coupling to some other proton, although all other signals appeared as singlets. Selective irradiation of a proton at 7.31 ppm led to moderate sharpening of this peak (about 2.6 ppm) and change into a triplet (J=6 Hz). In addition, the irradiation of the doublet (4.66 ppm) led to the collapse of the exchangeable proton into a broad singlet, as it was expected. The $^1$H NMR of metabolite IB contained only one other signal at 5.22 ppm, integrating to two protons.

Close similarities between IA and IB were also observed in the $^{13}$C NMR spectra. A total of eleven car- Taking into consideration all of the above data the structure of 4-(hydroxymethyl)-7-methoxy-6- methyl-1(3H) isobenzofuranone was proposed for metabolite IB. However, further investigation into this structure was felt necessary in order to be certain of this assignment.

The results obtained from the NO experiments and given in Table 5 on metabolite IB were consistent with the proposed structure. Strong positive NOE effects were observed between H5--H9 and H8--H5. Saturation of the C-8 protons (4.66 ppm) gave strong enhancement of the H5 signal but only a moderate amount of enhancement of the methyl signal (H9). Very weak; effects were found between the methyl and the methoxy groups as well as the C-3 protons and the methoxy. This latter effect could be due to the conformation where the methoxy substituent is away from both the methyl and the neighboring carboxyl and hence, over the plane of the ring and possibly within NOE distance from the C-3 protons.

TABLE 5

Nuclear Overhauser Enhancement (NOE) in the ¹H NMR (300 MHz, acetone-d₆) spectrum of metabolite IB

| Saturated Signal (δ) | Observed Enhancement (δ) |
|---|---|
| 2.28 (9-CH3) | 3.98 (10-OCH3, 2%), 7.48 (H5, 6%) |
| 3.98 (10-OCH3) | 2.28 (9-CH3, <2%), 7.48 (H5, <2%) |
| 4.68 (2xH8) | 7.48 (H5, 12%), 5.33 (2xH3, 3%) |
| 5.33 (2xH3) | 4.68 (2xH8, <2%), 3.98 (—OCH3, <2%) |
| 7.48 (H5) | 2.28 (9-CH3, 5%), 4.68 (2xH8, 2%) |

The coupled $^1H-^{13}C$ NMR spectrum of metabolite IB did not show any long-range coupling between the C-3 protons and the lactone carbonyl. However, even with metabolite IA the $^3J$ value observed between C-1 and H3 was very small. The values of $^2J$ and $^3J$ coupling constants are greatly affected by the conformation of a molecule and the dihedral angles involved, hence, some differences between the two compounds were to be expected. The splitting patterns of the C-3a and the C-5 carbons were more complex in this case than for metabolite IA due to extra coupling with the C-8 protons. In the fully coupled spectrum C-3a appeared as a multiplet and C-5 as a doublet of multiplets. Selective decoupling of the two C-8 protons led to a change of the C-3a signal to a doublet ($^3J_{C-H5}=8.4$ Hz ) and the C-5 signal to a doublet of quartets, analogous to that observed with metabolite IA. The C-4 signal wa also affected (became much sharper) indicating a small $^2J$ coupling with the C-8 protons. Decoupling of H5 had no effect on C-4 but changed the C-3a signal into a very narrow multiplet, or a triplet with a very small coupling constant.

There were a number of other carbon signals which appeared coupled. A triplet ($^1J=155$ Hz) was observed for C-3 and a triplet of doublets ($^1J=139$ HZ, $^3J=12$ Hz) for C-8. The latter signal changed to a doublet ($^3J=12$ Hz) when the C-8 protons were decoupled and to a triplet ($^1J=139$ Hz) when H5 was decoupled. The remaining of the data was very similar to that obtained for metabolite IA and in agreement with the proposed structure of this compound (Table 6).

Finally, the $^{13}C$ NMR chemical shifts of the literature compound 5-hydroxy-4-(hydroxymethyl)-7-methoxy-6-methyl-1(3H)-isobenzofuranone, a metabolite of the fungus *Aspergillus duricaulis*, described by Achenbach et al (*Liebios Ann. Chem.*, 1985. 1596) were used in order to calculate the "theoretical" chemical shifts for metabolite IB. The results obtained using the substituent differences were approximately within 2 ppm of the experimental values a shown in Table 6.

Identification of the Metabolite 4-carboxy-7-methoxy-6-methyl-1(3H)-isobenzofuranone(IC)

Compound IC was one of the three metabolites of *P. convolvulus* to be isolated from the more polar components of crude Pc 5 (Table 1). As it was mentioned previously, partitioning of Pc 5 via a reverse phase flash column, followed by HPLC chromatography of fractions 20 and 21 gave pure metabolite IC as an amorphous white solid.

A methyl group at 2.34 ppm, a methoxy at 4.15 ppm and a single aromatic proton at 8.13 ppm w(e)re once again present in the ¹H NMR spectrum. An additional signal at 5.49 ppm (s, 2H) was the only major difference between this compound and metabolite IA.

The $^{13}C$ NMR spectra of this compound was nearly identical to that of IA with the exception of one carbon. When the spectra was recorded at room temperature, a sharp carbonyl signal at 168.4 ppm (lactone) and a very broad carbonyl signal at 166.4 ppm (carboxylic acid) were observed. An additional broad quaternary signal at 120.5 ppm was assigned to a carbon directly attached to the carboxylic acid. It should be noted that low temperature ($-52°$ C.) had the same sharpening effect on these two $^{13}C$ signals as it did with those of compound IA. The methoxy and methyl signals appeared at 62.6 and 15.6 ppm respectively and the aromatic =CH— carbon at 138.8 ppm. A low field signal at 161.2 ppm was, once again, assigned to the carbon carrying the methoxy substituent. The remaining three quaternary carbons at 150.7, 132.2 and 117.6 ppm corresponded closely to the carbons C-3a, C-6 and C-7a, respectively, of metabolite IA. The only major difference observed between the two compounds was in the chemical shift and substitution of the C-3 carbon. In metabolite IA this carbon appeared at 97.4 ppm (—O—CH—O—) where in IC it was a —CH₂— carbon at 70.9 ppm (as indicated by DEPT NMR). Such a structural change would also explain the differences observed in the ¹H NMR spectrum (a —O—CH₂— peak at 5.49 ppm in the spectrum of metabolite IC in the place of a single —O—CH—O— proton at 6.91 ppm in that of IA). Hence, the chemical structure of 4-carboxy-7-methoxy-6-methyl-1(3H)-isobenzofuranone was proposed for metabolite IC The IR data confirmed the presence of a carboxylic acid (OH at 3381, 3226 and C=O at 1728 cm⁻¹) and a conjugated five-member ring lactone (C=O at 1773, C=C at 1613 cm⁻¹). High resolution chemical ionization (NH₃) mass spectrometry gave a molecular ion of mass 223.0621 (M⁺ +1) supporting the elemental composition of $C_{11}H_{10}O_5$ (calculated mass for M⁺ +1 is 223.0606).

TABLE 6

$^{13}C$ NMR (300 MHz, acetone-d₆, −52° C.) of metabolite IB

| C | decoupled δ | calculated δ | coupled | H8 decoupling | H5 decoupling |
|---|---|---|---|---|---|
| 1 | 171.2 | ~170 | s | s | s |
| 7 | 157.7 | 155.4 | m | m | m |
| 3a | 146.7 | 144.6 | m | d; $^3J_{C-H5} = 8.4$ Hz | s(br) |
| 5 | 137.2 | 134.8 | d,m; $^1J = 156$ Hz | d,q; $^3J_{C-H9} = 5$ Hz | m |
| 6 | 132.7 | 132.1 | q; $^2J_{C-H9} = 6$ Hz | q | q |
| 4 | 131.2 | 128.1 | s | s | s |
| 7a | 117.8 | 116.3 | s | s | s |
| 3 | 70.1 | 68.4 | t; $^1J = 155$ Hz | t | t |
| 10 | 62.5 | 62.2 | q; $^1J = 145$ Hz | q | q |
| 8 | 62.1 | 59.8 | t,d; $^1J = 139$ Hz | d; $^3J_{C-H8} = 12$ Hz | t |
| 9 | 15.4 | — | d,q; $^1J = 128$ Hz $^3J_{C-H5} = 5$ Hz | d,q | q |

$^1H$—$^{13}C$ fully coupled and selectively decoupled NMR experiments were also carried out and all of the data obtained was in complete agreement with the proposed structure (Table 7). The assignment of each carbon was confirmed on the basis of its chemical shift and splitting pattern. The $^3J$ couplings noted between H5--C-9, H9--C-5, H5--C-3a and a very small $^2J$ coupling between H3--C-3a confirmed that the proposed ring substitution was correct.

$^{13}C$ chemical shifts of the literature compound 4-formyl-5-hydroxy-7-methoxy-6-methyl-1(3H)-isobenzofuranone were used to calculate "theoretical" shifts for metabolite IC. The results obtained were in close agreement with the actual values given in Table 7.

TABLE 7

| | $^{13}C$ NMR (300 MHz, acetone-$d_6$, $-52°$ C.) of metabolite IC | | | | |
|---|---|---|---|---|---|
| C | decoupled δ | calculated δ | H—C coupled | H3 decoupling | H5 decoupling |
| 1 | 168.4 | — | s(br) | s(sh) | s(br) |
| 8* | 166.4* | — | s(br) | s(br) | s(sh) |
| 7 | 161.2 | 162.0 | m | m | m |
| 3a | 150.7 | 153.1 | m | d, $^3J_{C-H5}$ = 7.8 Hz | s(br) |
| 5 | 138.8 | 140.3 | d,q; $^1J$ = 162 Hz | d,q | q, $^3J_{C-H9}$ < 5 Hz |
| 6 | 132.2 | 131.8 | q $^2J_{C-H10}$ = 6 Hz | q | q |
| 4* | 120.5* | 118.0 | s | s | s |
| 7a | 117.6 | 116.7 | s | s | s |
| 3 | 70.9 | ~68 | t $^1J$ = 159 Hz | s | t |
| 10 | 62.6 | 62.2 | q $^1J$ = 146 Hz | q | q |
| 9 | 15.6 | — | d,q; $^1J$ = 128 Hz $^3J_{C-H5}$ = ~4.5 Hz | d,q | q |

*broad signals at room temperature
sharpening of signal indicates the removal of coupling having a very small J value.

EXPERIMENTAL

General Methods

Reagents and Chemicals n-octadecyltrichlorosilane was purchased from Fluka Chemie AG. Doubly distilled water and HPLC grade methanol were filtered through a 0.45μ filter membrane (Millipore Corp., Bedford, Mass.) before using them for HPLC. All chromatographic solvents were fractionally distilled prior to use with the exception of acetic acid.

Chromatography

Reverse phase flash column chromatography was carried out on silica gel (Merck Kieselgel 60, 230-400 mesh, #9385) reacted With n-octadecyltrichlorosilane.

HPLC chromatography, analysis and purifications, were carried out on a Waters instrument (pump model 501, variable wavelength detector model 450, U6K injector). Two reverse phase C18 columns were used; Whatman Partisil 5 ODS 3 cm×9.4 mm ID, 5 mm particles, Chromatographic Specialties Inc.) and CSC-S ODS2 ( 25 cm×9.4 mm ID, 5 mm particles, Chromatography Science Company Inc., Montreal, Que.).

Spectra

Ultraviolet spectra were recorded on a Hewlett Packard 8451A DIODE ARRAY Spectrophotometer. Nuclear Magnetic Resonance spectra were obtained at 20°-22° C. (unless otherwise indicated) using Varian XL-200, XL-300 and Bruker 500 MHz instruments. $^1H$ and $^{13}C$-NMR chemical shifts are quoted in ppm and are referenced to the internal deuterated solvent downfield from tetramethylsilane (TMS). All mass spectra were performed at the Biomedical Mass Spectrometry Unit, McGill University. The low resolution chemical ionization (NH$_3$) spectra were obtained using a HP 5980A spectrometer. FAB and high resolution chemical ionization spectra (NH$_3$) were obtained using a ZAB 2F HS instrument.

General Extraction of Active Metabolites from *P. convolvulus*

Stock cultures of *P. convolvulus* (conidia) were maintained at 4° C. in slant tubes containing potato carrot agar, covered with mineral oil. An aqueous suspension of conidia was used to inoculate potato dextrose agar plates which were then incubated at room temperature for a period of 2-4 weeks. The new conidia were isolated by washing the surface of the agar plates with a small volume (5-10 mL/ plate) of sterile water. Large scale cultures were subsequently initiated by inoculating moist barley grains in Erlenmeyer flasks (150×250 mL flasks, 20 grams of grain plus 30 mL of H$_2$O in each) under aseptic conditions. The cultures were stored at room temperature, with only occasional shaking. After an incubation period of four weeks, 100 mL of H$_2$O were added to each flask and they were placed overnight on a rotary shaker. Filtration through several layers of cheese cloth and centrifugation at 5,000 rpm for 8 minutes led to the removal of barley grains, separation of new conidia and isolation of a biologically active aqueous mixture of metabolites (Pc 1).

The volume of Pc 1 (15 L) was reduced (3 L) under high vacuum at 30° C. and then freeze-dried to obtain 27 g of a very fine powder. This powder was extracted twice with methanol (2×1.5 L), the first time at 40° C. for three hours and the second time at room temperature overnight. The methanolic solution (Pc 2) was filtered through several layers of cheese cloth in order to remove the bulk of the undissolved matterial, which did not exhibit any biological activity. The remaining solid was removed by centrifugation, since the powder was too fine to be filtered.

The methanolic mixture of metabolites was evaporated to dryness and redissolved in 100 mL of water to obtain a cloudy suspension which was acidified to pH 2.5×3 with 0.1 M HCl. Ethyl acetate extraction (3×150 mL, plus overnight with 300 mL) led to the isolation of a biologically active crude (Pc 3), where the remaining aqueous mixture was found to be void of biological activity. The yields of the combined ethyl acetate extracts varied greatly (0.25-7.5 mg/g of barley) giving an average of 2.5 mg of the light brown gum (Pc 4) per gram of infected barley grains.

The active crude Pc 3 was suspended in CH$_2$Cl$_2$ (100 mL) and extracted with a saturated solution of NaH- CO₃ (3×100 mL) to partition the mixture into crudes Pc 4 and Pc 5. The organic layer (Pc 4) contained mostly steroidal metabolites exhibiting very weak phytotoxicity while the aqueous layer (Pc 5) was strongly phytotoxic and it contained a large mixture of compounds. The aqueous layer (Pc 5) was subsequently acidified to pH 2.5-3 with 0.1 M HCl, reduced in volume under high vacuum at 30° C. and extracted with ethyl acetate (3×100 mL) in order to recover the phytotoxic mixture of metabolites in Pc 5.

Isolation of Phytotoxic Metabolites IA, IB and IC from Crude pc 5 of *P. convolvulus*

Preparation of C18 reverse-phase silica gel

Silica gel (40 g, Merck Kieselgel 60, 230-400 mesh) was added to 300 mL dry CCl₄ (redistilled from P₂O₅) in a septum-capped round bottom flask under a nitrogen atmosphere. n-octadecyltrichlorosilane (4 mL) was added and the suspension was stirred at room temperature for two hours.

The product was filtered into a dry seinterglass funnel and washed free of unreacted silane with dry CCl₄ (3×100 mL). Any residual chloride substituents were converted to methoxy groups by washing the silica with dry methanol (2×100 mL, redistillied over Mg metal). The product was then quickly washed with with dry CH₂Cl₂ (2×100 mL, redistilled from P₂O₅) and allowed to briefly dry under vacuum.

A fresh 300 mL volume of dry CCl₄ was added to the bonded silica along with 4 mL of trimethylchlorosilane. The mixture was stirred at room temperature for an additional two hours, then filtered and washed with dry CH₂Cl₂ (3×100 mL). The bonded silica was dried at 40° C. overnight and under high vacuum for a day.

Reverse phase flash column chromatography of phytotoxic crude Pc 5

A reverse phase silica gel column (12 mm×32 cm) was packed as a methanolic slurry (12 g C18 bonded silica) and then very slowly equilibrated with H₂O.

The crude Pc 5 (1.3 q) was dissolved in a mixture of H₂O/ CH₃OH/ CH₂Cl₂, and absorbed onto a small amount of C18 bonded silica gel (1-2 g) by evaporating off the organic solvents. The aqueous slurry obtained (5-10 mL) was added to the top of the reverse phase column and eluted with the gradient of solvents described in Table 2 at a flow rate of about 1″/min. All fractions (20 mL each) were tested for biological activity. Strong phytotoxicity was observed with fractions 6, 7 and 8 which were further purified by HPLC.

A new sample of Pc 5 (1.2 g) was chromatographed using a reverse phase column as described above. Smaller fractions (8 mL each) were collected and compared with the previously isolated active crudes (fractions 6, 7 and 8) by TLC.

Metabolites IA and IB were isolated from fractions 18 and 19 after HPLC chromatography on a C18 reverse phase column, using an eluent mixture of 59.8% H₂O, 40% CH₃OH and 0.2% CH₃COOH at a flow rate of 2 mL/min. The retention time of IA was 22-23 minutes after the void volume where that of IB was 16-17 minutes. Metabolite IB was rechromatographed on the same HPLC column using a solvent mixture of 54.1% H₂O, 45.8% CH₃OH and 0.1% CH₃COOH. At a flow rate of 2 mL/min its elution time was 10-11 minutes after the void volume. HPLC chromatography of fractions 20 and 21, on the same C18 reverse phase column using 54.4% H₂O, 45.4% CH₃OH and 0.2% CH₃COOH as the eluting solvent, led to the isolation of metabolite IC. At a flow of 2 mL/min, its retention time was 27-29 minutes from the void volume.

Identification data 4-carboxy-3-hydroxy-7-methoxy-6-methyl-1(3H)-isobenzofuranone (IA)

TLC: CH₂Cl₂/EtOAc/CH₃COOH (5:5:0.2), Rf=0.24.

IR (CH₃CN): 3381, 3226 (OH), 1773 (C=O, lactone), 1728 (C=O, carboxylic acid), 1613 (C=C) cm⁻¹.

UV (CH₃CH₂OH, nm): max 220, 250 (shd), min 300.

¹H NMR (200 MHz, acetone-d₆) δ: 2.35 (s, 3H, 9—CH₃), 4.14 (s, 3H, 10—OCH₃), 6.91 (s, 1H, H3) and 8.09 (s, 1H, H5) ppm.

NOE: data given in Table 3.

¹³C NMR (300 MHz, acetone-d₆, T=−46.5° C.) δ: 15.7 (C-9), 62.6 (C-10), 97.4 (C-3), 118.3 (C-7a), 121.9 (C-4), 134.3 (C-6), 139.3 (C-5), 149.4 (C-3a), 160.5 (C-7), 165.7 (C-8) and 166.4 (C-1) ppm.

Coupled ¹H-¹³C NMR: data given in Table 4.

APT (D2=4 msec) NMR (300 MHz, acetone-d₆, T=−46.5° C.) δ: 118.3, 121.9, 134.3, 149.4, 160.5, 165.7 and 166.4 ppm (97.4, 139.3 ppm tertiary carbons).

MS [C.I. (NH₃), direct inlet, 260° C.]: m/z (% relative intensity, assignment): 256 (100, M⁺+NH₃), 239 (53, M⁺+1), 227 (56, M⁺+NH₃−CHO), 209 (15, M⁺−CHO).

4-(Hydroxymethyl)-7-methoxy-6-methyl-1(3H)-isobenzofuranone (IB)

TLC CH₂Cl₂/EtOAc/CH₃COOH (5:5:0.2), Rf=0.38.

IR (CH₃CN): 3630, 3540 (OH), 1762 (C=O, lactone), 1600 (C=C) cm⁻¹.

UV (CH₃CH₂OH, nm): max 212, 238 (shd), min 300.

¹H NMR (300 MHz, CDCl₃, T=−51.5° C.) δ: 2.26 (s, 3H, 9—CH₃) 2.6-2.7 (br, 1H, C—8 OH)¹, 3.90 (s, 3H, 10—OCH₃), 4.66 (d, J=6 Hz, 2H, H8), 5.22 (s, 2H, H3) and 7.31 (s, 1H, H5)² ppm.

[1] D₂ exchange causes the disappearance of this signal, as expected, and the collapsing of the doublet at 4.66 ppm to a singlet. [2] Decoupling of H5 led to the change of the OH signal from a broad multiplet to a broad triplet (J$_{H8-)H}$=6Hz), indicating the presence of long range coupling between h5 and OH.

NOE: data given in Table 5

¹³C NMR (300 MHz, CD₃OD)δ: 15.4 (C-9), 62.2 (C-8), 62.5 (C-10), 70.1 (C-3), 117.9 (C-7a), 132.2 (C-4), 132.7 (C-6), 137.2 (C-5), 146.7 (C-3a), 157.7 (C-7) and 171.2 (C-1) ppm.

Coupled ¹H-¹³C NMR data given in Table 6.

A further active metabolite active against *Lemna paucicostata* was isolated from the fungus *Phomopsis convolvulus*, and which was isolated from crude Pc 5 is the 3-(4-methoxy-3-methyl-α-pyron-6-yl)2-methyl-2-butenoic acid of formula II.

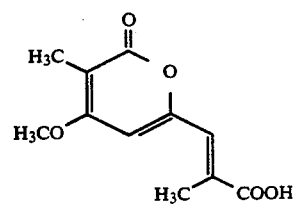

The structural assignment of the compound of formula II was based on its spectral data and it was found to be weakly phytotoxic to both Lemna plants and field bindweed.

TLC CH$_2$Cl$_2$/EtOAc/CH$_3$COOH (5:5:0.2), Rf=0.33

IR(CH$_3$CN) 3628, 3618 (OH), 1717 (C=O,α-pyron), 1707,1702 (sh) (C=O carboxylic acid) cm$^{-1}$.

UV (CH$_3$CH$_2$OH,nm): max 238, min 340

$^1$H NMR (200 MHz, acetone-d$_6$) δ: 1.87 (s, 3H, C—3'—CH$_3$); 2.42 (s, 3H, C—2—CH$_3$); 4.04 (s, 3H, C—4'—OCH$_3$); 6.62 (s, 1H, H3); and 6.91 (s, 1H, H5') ppm.

NOE NMR: data given in Table 8.

$^{13}$C NMR (300 MHz, CD$_3$OD) δ: 8.8 (C—3'—CH$_3$); 13.6 (C—2-CH$_3$); 57.5 (C—4'—OCH$_3$); 98.4 (C—5'); 105.3 (C—3'); 121.8 (C—3); 143.2 (C-2); 159.2 (C-6'); 166.4 (C-4'); 167.90 (C-2'); and 169.4 (br. C-1) ppm.

Coupled $^1$H—$^{13}$C NMR (400 MHz, CD$_3$OD) δ: 8.8 (m, C-3'—CH$_3$); 13.6 (q, J=129 Hz, C-2—CH$_3$); 57.5 (q, J=147 Hz, C-4'—OCH$_3$); 98.4 (d, J=170 Hz, C-5'); and 121.8 (d, J=165 Hz, C-3) ppm.

APT (D2=4 msec) NMR (300 MHz, CD$_3$OD) δ: 105.3, 143.2 159.9, 166.4, 167.9, and 169.4 (98.4, 121.8 ppm, tertiary carbons).

MS (high resolution, C.I. (NH$_3$), direct inlet, 250° C.): m/z calculated for the (M$^+$+1) ion 225.0763 found: 225,0739.

TABLE 8

| Nuclear Overhauser Enhancement in the $^1$H NMR Spectrum of metabolite II | |
|---|---|
| Saturated signals (δ) | Observed enhancement |
| 2.42 (—CH$_3$) | 6.91 (H, 10%) |
| 4.04 (—OCH$_3$) | 6.91 (H, 12%) |
| 6.91 (H) | 4.04 (—OCH$_3$, 4%), 2.42 (—CH$_3$, 3%) |

We claim:

1. A isobenzofuranone derivative which is 4-carboxy-3-hydroxy-7-methoxy-6-methyl-1(3H)-isobenzofuranone.

2. A method for destroying the undesirable pest Convolvulus arvensis (field bindweed) and other weed species of the Convolvulaceae family which comprises the application of an effective amount of at least one compound of formula I:

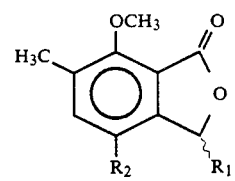

wherein R$_1$ is selected from hydrogen and hydroxy and R$_2$ is selected from —CH$_2$OH and —COOH, and mixtures thereof, and agriculturally acceptable salts and esters thereof, with the proviso that when R$_1$ is hydroxy R$_2$ is —COOH, in association with an inert carrier onto said undesired vegetation or onto the situs of said undesired vegetation.

3. The method of claim 2 wherein the active compound is 4-carboxy-3-hydroxy-7-methoxy-6-methyl-1 (3H)-isobenzofuranone.

4. The method of claim 2 wherein the active compound is 4-(hydroxymethyl)-7-methoxy-6-methyl-1(3H)-isobenzofuranone.

5. The method of claim 2 wherein the active compound is 4-carboxy-7-methoxy-6-methyl-1(3H)-isobenzofuranone.

6. A herbicidal composition characterized by its ability to induce toxic symptoms to the agricultural pest Convolvulus arvensis (field bindweed) and other weed species in the Convolvulaceae family, which comprises, as the active ingredient, the compound of claim 1, and agriculturally acceptable salts and esters thereof, in association with an inert carrier.

7. A method according to claim 2, wherein said compound is applied as a spray.

8. A method according to claim 2, wherein said compound is applied as an aqueous solution.

* * * * *